(12) United States Patent
Helm et al.

(10) Patent No.: US 12,629,099 B2
(45) Date of Patent: May 19, 2026

(54) STATISTICAL DEPENDENCE-AWARE BIOLOGICAL PREDICTIVE SYSTEM

(71) Applicant: Microsoft Technology Licensing, LLC, Redmond, WA (US)

(72) Inventors: Hayden Sullivan Helm, Salem, VA (US); Guodong Chen, Baltimore, MD (US); Weiwei Yang, Seattle, WA (US); Kateryna Lytvynets, Redmond, WA (US)

(73) Assignee: Microsoft Technology Licensing, LLC

( * ) Notice: Subject to any disclaimer, the term of this patent is extended or adjusted under 35 U.S.C. 154(b) by 1189 days.

(21) Appl. No.: 17/553,063

(22) Filed: Dec. 16, 2021

(65) Prior Publication Data

US 2023/0190204 A1 Jun. 22, 2023

(51) Int. Cl.
*G06N 3/04* (2023.01)
*A61B 5/00* (2006.01)
(Continued)

(52) U.S. Cl.
CPC ............ *A61B 5/7264* (2013.01); *A61B 5/372* (2021.01); *G06F 18/2134* (2023.01);
(Continued)

(58) Field of Classification Search
CPC ....... A61B 5/7264; A61B 5/372; A61B 5/318; A61B 5/369; A61B 5/7267; A61B 5/4884; A61B 5/165; G06F 18/2134; G06F 18/214; G06F 18/22; G06F 2218/10; G06F 18/213; G06F 18/2131; G06F 18/15; G06F 18/2135; G06N 20/00
See application file for complete search history.

(56) References Cited

U.S. PATENT DOCUMENTS 10,504,020 B2 * 12/2019 Trenholm .............. G06N 3/045
11,205,420 B1 * 12/2021 Fu ............................ G06N 3/04
(Continued)

FOREIGN PATENT DOCUMENTS

CN 113705715 B * 4/2024 ......... G06F 18/2415
ES 2975078 T3 * 7/2024 ........... A61B 5/7246
(Continued)

OTHER PUBLICATIONS

Chen, et al., "Mental State Classification Using Multi-Graph Features", In Journal of Frontiers in Human Neuroscience, vol. 16, Jul. 8, 2022, 12 Pages.
(Continued)

*Primary Examiner* — Hassan Mrabi
(74) *Attorney, Agent, or Firm* — Schwegman Lundberg & Woessner, P.A.

(57) ABSTRACT

A computer implemented method includes accessing a multivariate time series set of samples collected by multiple biological sensors sensing a first biological function over a first period of time, dividing the data set into windows, calculating statistical dependencies between the samples of the timeseries data collected by each sensor, generating a relationship matrix as a function of the statistical dependencies, and transforming the relationship matrix to generate a first feature vector for each window of time that captures the statistical dependencies amongst the sensors.

16 Claims, 4 Drawing Sheets

(51) Int. Cl.

| | | |
|---|---|---|
| *A61B 5/372* | (2021.01) | |
| *G06F 18/2134* | (2023.01) | |
| *G06F 18/214* | (2023.01) | |
| *G06F 18/22* | (2023.01) | |
| *G06N 20/00* | (2019.01) | |

(52) U.S. Cl.
CPC ............ *G06F 18/214* (2023.01); *G06F 18/22* (2023.01); *G06N 20/00* (2019.01)

(56) References Cited

U.S. PATENT DOCUMENTS

| | | | | |
|---|---|---|---|---|
| 2006/0015263 A1* | 1/2006 | Stupp | ...................... | G06F 17/18 |
| | | | | 702/19 |
| 2012/0310050 A1* | 12/2012 | Osorio | ................... | G16H 20/40 |
| | | | | 600/300 |
| 2013/0096839 A1* | 4/2013 | Osorio | ................... | A61B 5/726 |
| | | | | 702/19 |
| 2013/0231949 A1* | 9/2013 | Baronov | ................ | G16H 50/30 |
| | | | | 705/2 |
| 2016/0228705 A1* | 8/2016 | Crowder | ............ | A61N 1/36064 |
| 2017/0270919 A1* | 9/2017 | Parthasarathi | .......... | G10L 17/06 |
| 2019/0209022 A1* | 7/2019 | Sobol | ...................... | A61B 5/681 |
| 2020/0004655 A1* | 1/2020 | Abrami | ................... | G06N 20/00 |
| 2020/0222010 A1* | 7/2020 | Howard | ................... | G06N 5/02 |
| 2020/0234582 A1* | 7/2020 | Mintz | ............. | G08G 1/096811 |
| 2020/0322703 A1* | 10/2020 | Bures | ...................... | G06F 16/27 |
| 2020/0405204 A1* | 12/2020 | Howard | ............. | A61B 5/14546 |
| 2021/0169417 A1* | 6/2021 | Burton | ................. | A61B 5/4857 |
| 2021/0236044 A1* | 8/2021 | Arroyo-Gallego | .... | A61B 5/112 |
| 2021/0365762 A1* | 11/2021 | Rafey | ................... | G16Y 40/10 |
| 2022/0007965 A1* | 1/2022 | Tiron | ................... | A61B 5/0823 |
| 2023/0022710 A1* | 1/2023 | Aubin | ..................... | G06F 30/20 |
| 2024/0070251 A1* | 2/2024 | Maizels | ................. | G10L 13/02 |
| 2025/0038765 A1* | 1/2025 | Galvin | ............... | H03M 7/6005 |
| 2025/0235114 A1* | 7/2025 | Russek-Sobol | ......... | H04W 4/38 |

FOREIGN PATENT DOCUMENTS

| | | | | | | |
|---|---|---|---|---|---|---|
| JP | | 5301717 | B1 * | 9/2013 | .......... | G05B 23/024 |
| JP | | 2019505011 | A * | 2/2019 | ............ | G06V 40/16 |
| JP | | 7296503 | B2 * | 6/2023 | .......... | A61B 5/7225 |
| JP | | 7479711 | B2 * | 5/2024 | ............ | G10L 25/66 |
| KR | | 20220135943 | A * | 10/2022 | ........ | H04L 12/2827 |
| WO | WO-2005067790 | A1 * | 7/2005 | ............ | A61B 5/412 |
| WO | WO-2007075477 | A2 * | 7/2007 | ........ | A61N 1/36064 |
| WO | WO-2014078859 | A1 * | 5/2014 | ............ | G16H 40/63 |
| WO | WO-2017201323 | A1 * | 11/2017 | ............ | G16H 50/30 |
| WO | WO-2019165079 | A2 * | 8/2019 | .......... | G05B 23/024 |
| WO | WO-2020089382 | A1 * | 5/2020 | ............ | G16H 20/10 |
| WO | WO-2020190295 | A1 * | 9/2020 | .......... | G06F 3/0604 |
| WO | WO-2021234037 | A1 * | 11/2021 | .......... | A61B 5/4818 |

OTHER PUBLICATIONS

Li, et al., "Graph Signal Processing, Graph Neural Network and Graph Learning on Biological Data: A Systematic Review", In Journal of IEEE Reviews in Biomedical Engineering, vol. 16, Oct. 26, 2021, pp. 109-135.

"International Search Report and Written Opinion Issued in PCT Application No. PCT/US22/052064", Mailed Date: Apr. 20, 2023, 12 Pages.

Xing, et al., "Altered Dynamic Electroencephalography Connectome Phase-Space Features of Emotion Regulation in Social Anxiety", In Journal of Neuroimage, vol. 186, Feb. 1, 2019, pp. 338-349.

Zhang, et al., "Fatigue Detection With Covariance Manifolds of Electroencephalography in Transportation Industry", In Journal of IEEE Transactions on Industrial Informatics, vol. 17, Issue 5, May 2021, pp. 3497-3507.

Communication pursuant to Article 94(3) Received in European Patent Application No. 22851073.1, mailed on Oct. 21, 2025, 09 pages.

Jin, et al., "Interpretable Cross-Subject EEG-Based Emotion Recognition Using Channel-Wise Features", Sensors, vol. 20, Issue 23, Nov. 24, 2020, pp. 750-762.

* cited by examiner

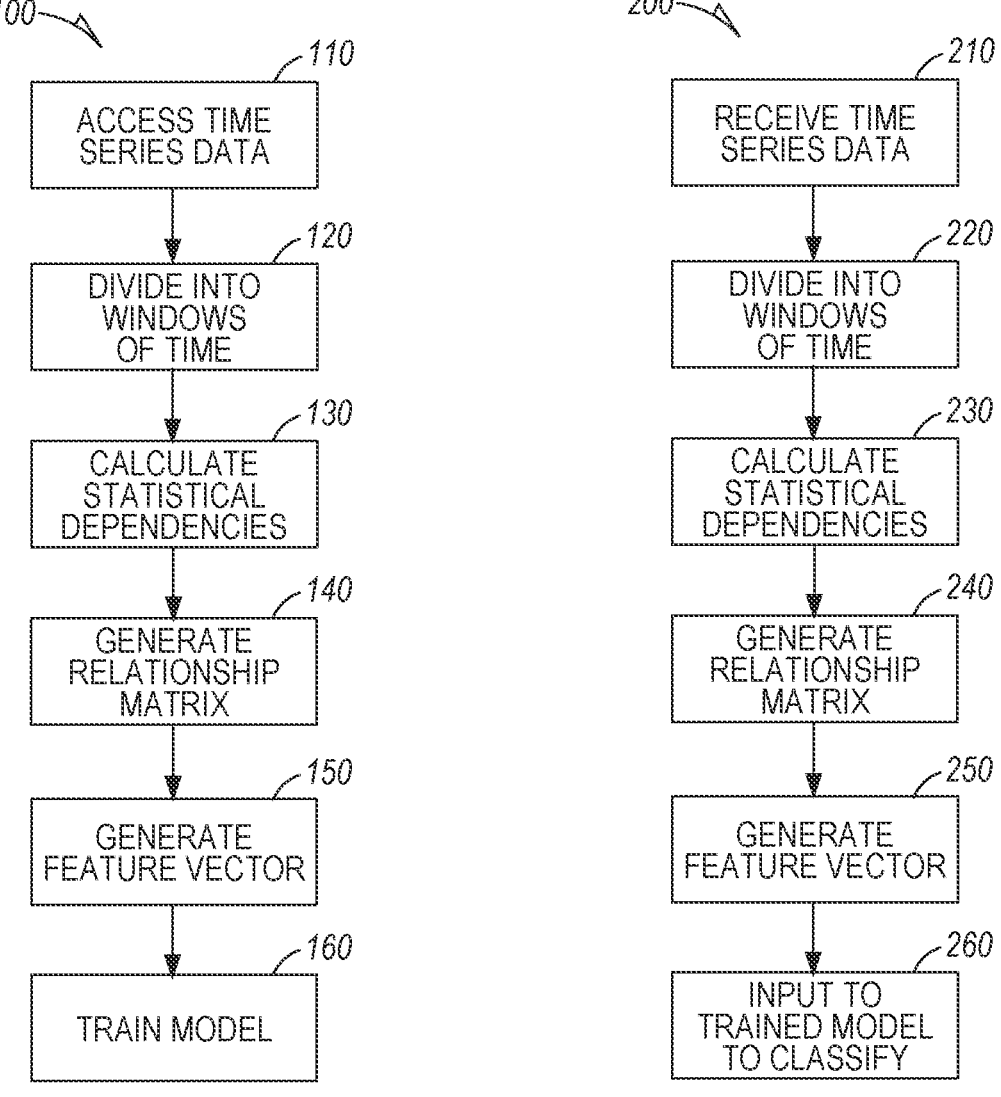
*FIG. 1*          *FIG. 2*

STATISTICAL DEPENDENCE-AWARE BIOLOGICAL PREDICTIVE SYSTEM

BACKGROUND

Machine learning systems can be used to recognize patterns that humans cannot. The input to such systems, referred to as an original signal, can include a large amount of sensed data, making it computing resource intensive to process. To reduce the amount of processing needed, features can first be extracted from the input. The extraction of such features in an efficient manner can be technically challenging.

SUMMARY

A computer implemented method includes accessing a multivariate time series set of samples collected by multiple biological sensors sensing a first biological function over a first period of time, dividing the data set into windows, calculating statistical dependencies between the samples of the timeseries data collected by each sensor, generating a relationship matrix as a function of the statistical dependencies, and transforming the relationship matrix to generate a first feature vector for each window of time that captures the statistical dependencies amongst the sensors. The method may be used in a prediction system that includes suitable hardware.

BRIEF DESCRIPTION OF THE DRAWINGS

FIG. 1 is a flowchart illustrating a computer implemented method of generating efficient feature vectors representing a multi-variate time series data set for training a machine learning model according to an example embodiment.

FIG. 2 is a computer implemented method of using a trained machine learning model to classify input data according to an example embodiment.

Figure 3:
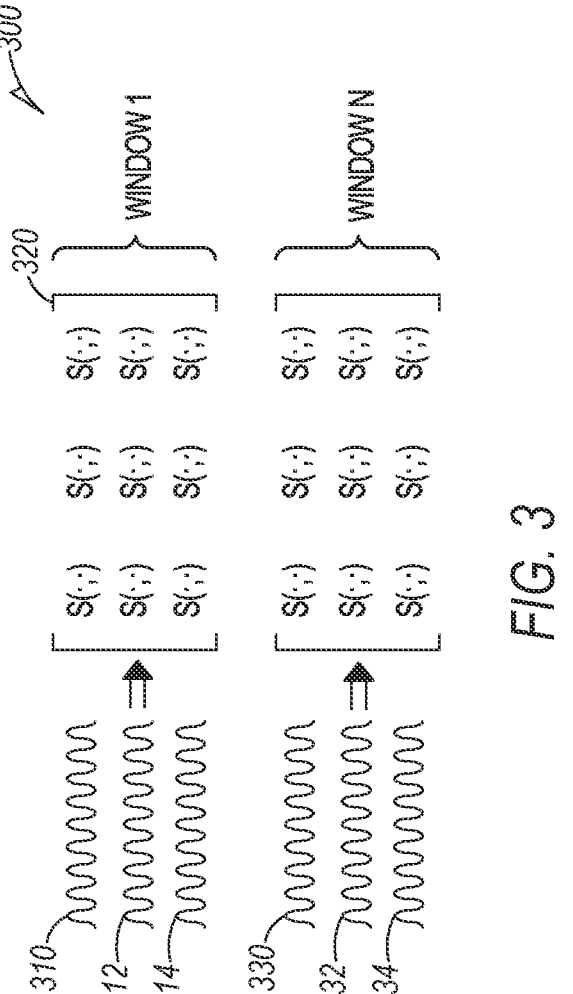
FIG. 3 is a block flow diagram showing first feature extraction used is based on a correlation structure amongst sensors according to an example embodiment.

DETAILED DESCRIPTION in the following description, reference is made to the accompanying drawings that form a part hereof, and in which is shown by way of illustration specific embodiments which may be practiced. These embodiments are described in sufficient detail to enable those skilled in the art to practice the invention, and it is to be understood that other embodiments may be utilized and that structural, logical and electrical changes may be made without departing from the scope of the present invention. The following description of example embodiments is, therefore, not to be taken in a limited sense, and the scope of the present invention is defined by the appended claims.

The functions or algorithms described herein may be implemented in software in one embodiment. The software may consist of computer executable instructions stored on computer readable media or computer readable storage device such as one or more non-transitory memories or other type of hardware-based storage devices, either local or networked. Further, such functions correspond to modules, which may be software, hardware, firmware or any combination thereof. Multiple functions may be performed in one or more modules as desired, and the embodiments described are merely examples. The software may be executed on a digital signal processor, ASIC, microprocessor, or other type of processor operating on a computer system, such as a personal computer, server or other computer system, turning such computer system into a specifically programmed machine.

The functionality can be configured to perform an operation using, for instance, software, hardware, firmware, or the like. For example, the phrase "configured to" can refer to a logic circuit structure of a hardware element that is to implement the associated functionality. The phrase "configured to" can also refer to a logic circuit structure of a hardware element that is to implement the coding design of associated functionality of firmware or software. The term "module" refers to a structural element that can be implemented using any suitable hardware (e.g., a processor, among others), software (e.g., an application, among others), firmware, or any combination of hardware, software, and firmware. The term, "logic" encompasses any functionality for performing a task. For instance, each operation illustrated in the flowcharts corresponds to logic for performing that operation. An operation can be performed using software, hardware, firmware, or the like. The terms, "component," "system," and the like may refer to computer-related entities, hardware, and software in execution, firmware, or combination thereof. A component may be a process running on a processor, an object, an executable, a program, a function, a subroutine, a computer, or a combination of software and hardware. The term, "processor," may refer to a hardware component, such as a processing unit of a computer system.

Furthermore, the claimed subject matter may be implemented as a method, apparatus, or article of manufacture using standard programming and engineering techniques to produce software, firmware, hardware, or any combination thereof to control a computing device to implement the disclosed subject matter. The term, "article of manufacture," as used herein is intended to encompass a computer program accessible from any computer-readable storage device or media. Computer-readable storage media can include, but are not limited to, magnetic storage devices, e.g., hard disk, floppy disk, magnetic strips, optical disk, compact disk (CD), digital versatile disk (DVD), smart cards, flash memory devices, among others. In contrast, computer-readable media, i.e., not storage media, may additionally include communication media such as transmission media for wireless signals and the like.

A computer implemented method includes accessing a multivariate time series set of samples collected by multiple biological sensors sensing a first biological function over a first period of time, dividing the data set into windows, calculating statistical dependencies between the samples of the timeseries data collected by each sensor, generating a distance matrix as a function of a relationships between the statistical dependencies, and transforming the relationship matrix to generate a first feature vector for each window of time that captures the statistical dependencies amongst the sensors. The method may be used in a prediction system that includes suitable hardware.

High-level mental states such as fatigue, cognitive load, and stress can adversely affect safety and productivity. Brain-Computer Interfaces (BCIs) can theoretically provide real-time indicators of high-level mental states and actively suggest mitigating measures. Recent advances in electroencephalography (EEG) hardware quality and affordability have made understanding the relationship between signals from the brain and high-level mental states useful for non-lab settings in real time. Advances in other types of biosensing such as electrocardiograms (ECG) and electrocartiography (ECoG) have similarly made it possible to transfer lab-developed knowledge of the correlation between biosignals and high-level mental states to the real world.

Devices that capture human biosignals such as EEG, ECG, ECoG, and heart rate monitors are becoming pervasive as we begin to adopt wearable and everyday technological devices. Learning how to uncover relevant signal from data from these devices will enable a smoother interaction between the device and the wearer that will ultimately improve the wearer's daily life. Further, combining these biosensing technologies into a single system will enable even greater predictive precision.

These devices often have multiple sensors that collect data on a regular interval. This type of regular data collection from multiple sensors is referred to as a multi-variate time series.

Machine learning systems can use previously seen multi-variate time series to learn a function that takes as input a multi-variate time series and outputs a relevant prediction. In some cases, a relevant prediction is a class label that can represent stress or fatigue. In other cases, a relevant prediction is the direction of a hand movement.

The effectiveness of a machine learning system (measured by how well it makes predictions) is oftentimes directly related to the quality of the signal it is trained on. For example, most machine learning systems cannot make a reasonable prediction based on the originally collected multi-variate time series alone. Feature extraction techniques are thus used to simplify the signal so that the system can make better predictions on previously unseen examples.

The use of machine learning systems in biological processing is heavily dependent on extracting features from the collected multi-variate time series.

Traditionally, the feature extraction techniques are done on a sensor by sensor basis. For example, in EEG processing a single time series is broken down into its composite frequency bands that are neuroscientifically relevant. Once the original signal is broken down into bands, the power of the signal in each band is recorded as a vector of powers. The vector of powers is considered a feature vector for that particular sensor. Analogous processes are used when processing other biosignal data. Sensor by sensor feature extraction ignores the statistical dependence between the sensors.

The process described herein is a machine learning system that directly leverages the collection of pairwise statistical dependences amongst sensors.

FIG. 1 is a flowchart illustrating a computer implemented method 100 for generating feature vectors representing a multi-variate time series as input to a machine learning model. Method 100 begins at operation 110 by accessing data collected from multiple sensors, such as biosensors, over a first period of time.

The data is divided at operation 120 into multiple, smaller time windows. The number of windows and their overlap may be dependent on each different application.

Operation 130 calculates the statistical dependence between the data collected by each of the multiple sensors for each of the time windows. Here, "statistical dependence" includes but is not limited to Pearson's correlation, mutual information, and conditional entropy. The output of Operation 130 is a collection of statistical dependence matrices, one corresponding to each of the time windows described. For time window, W, its corresponding statistical dependence matrix is denoted as M_(W).

Operation 140 generates a relationship matrix, such as a distance matrix, D, based on the distance between each pair of the matrices $M_{1}, \ldots, M_{W}$. Operation 140 also includes any pre-processing of the matrices, either jointly or individually, before measuring the distance between them. Here, distance includes but is not limited to the Frobenius norm of the difference between pairs of matrices and the spectral norm of the difference between pairs of matrices. Let D be the described distance matrix.

Operation 150 transforms D. Here, a transformation includes but is not limited to multi-dimensional scaling and random projections. One output of Operation 150 is a collection of vectors in m-dimensional space, one corresponding to each of the time windows. Here, m is data and application dependent. Let $v_{w}$ be the feature vector corresponding to window w.

Finally, Operation 160 trains a machine learning model using the learned feature vectors, also referred to as first feature vectors. In some instances, training the model requires a supervised signal such as a categorical label or position.

The final output of the process described in FIG. 1 is a machine learning system trained on features derived from the statistical dependence of biosensors.

In one example, second feature vectors may be generated based on power associated with frequency bands of the samples and used in combination with the first feature vectors to train a machine learning model based on the first and second feature vectors comprising training data. The training data includes labels from the accessed samples, which may include biological data from humans such as EEG and ECG data.

The first feature set in one example is derived from a correlation structure across multiple sensors. In addition to the first feature set, a second feature set may be derived from classical frequency band power analysis of collected multi-variate time signals.

In one example, two related complementary feature sets may be combined. The combination of these two feature extraction methods provides superior (supervised and semi-supervised) classification on a large-scale biological data set such as an electroencephalography (EEG) based Brain-Computer Interfaces (BCI) EEG data set that is publicly available.

Feature extraction may be performed by applying spectral graph embedding techniques on temporal correlations between EEG sensors. Connectivity and correlation-adjacent features such as synchronization between signals from different sensors have been explored, but the choice of different sensors to measure coupling strength is highly subjective and requires neurophysiological a priori knowledge. Recent research has also investigated representing EEG signals as matrices. This approach often needs a reference matrix to derive the kernel on the Riemannian space. The choice of reference matrix is either subjective or computationally intensive using a data-driven, adaptive method.

In one example of the system's utility, the system was compared to an existing system for predicting the stress of participants in a lab-controlled study. For each participant in the study, there are two EEG recordings—one corresponding to a resting state and one corresponding to a stressed state. For the resting state, participants counted mentally (i.e., without speaking or moving their fingers) with their eyes closed for three minutes. For the stressful state, participants were given a four-digit number (e.g., 1253) and a two-digit number (e.g., 43) and asked to recursively subtract the two-digit number from the four-digit number for 4 minutes. This type of mental arithmetic is known to induce stress.

The study included 66 participants (47 women and 19 men) of matched age in the study. 30 participants were excluded from an analysis due to poor EEG quality resulting in a set of 36 participants. The EEG data may be preprocessed via a high-pass filter and a power line notch filter. The task of interest is to classify whether an EEG segment is recorded during the resting state or stress state.

FIG. 2 is a flowchart illustrating a computer implemented method 200. Method 200 assumes it has access to the machine learning system trained in method 100, method 200 generates analogous feature vectors described in method 100 but for previously unseen segments of a multi-variate time series collected by biosensors.

Operation 210 receives the new multi-variate time series from the biosensors.

Operation 220 divides these times series into windows in an analogous fashion to operation 120. Assume that there are W' windows in the new time series.

Operation 230 generates the statistical dependence between the biosensors for each time window as in operation 130. For time window w denote its corresponding statistical dependence matrix as M'_{w}.

Operation 240 generates a relationship matrix, such as a distance matrix D' based on the distance from each of the matrices M'_{1}, . . . , M'_{W'} to each of the matrices M_{1}, . . . , M_{W}. The definition of distance is the same as in operation 140. Denote the new matrix as D'.

Operation 250 transforms D' to generate output feature vectors are that are comparable to the feature vectors generated by operation 150. That is, operation 250 outputs a feature vector for each time window described in Operation 220.

Operation 260 takes the vectors from operation 250 and the machine learning system from operation 160 to make a prediction for each of the vectors from operation 250.

Together, method 100 and method 200 form a machine learning system that is trained on features from a multi-variate time series of data from a set of biosensors and can make predictions related to previously unseen features.

The features derived from the pairwise statistical dependence of the sensors may be used in a more general machine learning system. Indeed, combining the features used in method 100 and method 200 with more local features like those derived from individual sensor data can greatly improve performance.

As with the method 100, feature vectors are generated from the input data. The input data is divided into non overlapping windows of time at operation 220, pairwise correlations between the input data collected by the multiple sensors for each window of time are determined at operation 230, a distance matrix is determined at operation 240 based on the differences between the pairwise correlations, and multidimensional scaling is performed at operation 250 to generate a first feature vector for each sample.

At operation 260, the input feature vectors are input to the machine learning model for classifying the input data.

FIG. 3 is a block flow diagram showing first feature extraction used is based on a correlation structure amongst sensors generally at 300. Time series data during a first window of time is shown from three sensors at 310, 312, and 314. Only data from three sensors is shown for simplicity. The number of sensors, N, in various examples may vary from 4 to 19 or more sensors.

For a particular window, the statistical dependence of the sensors is measured via some function "s". In one example, "s" may be a Pearson correlation, which is a measure between −1 and 1 where 1 means that if one of the signals "goes up" then the other signal "goes up" and −1 means that if one of the signals "goes down" then the other signal "goes up". In practice "s" could be any measure of statistical dependence (i.e. "Mutual Information", etc.) and so I tried to capture that in the illustration.

The statistical dependence is measured for each pair of sensors (hence the number-of-sensors by number-of-sensors matrix). The statistical dependences are measured for each time window.

Data for each window is shown as a matrix of functions "s" that measures the statistical dependence. Window I is shown at 320 and window N is shown at 325. The time series data for window N for the same three sensors is shown at 330, 332, and 334. As window N corresponds to a window of time that does not overlap with the first window of time, the signals may likely appear different.

Figure 4:
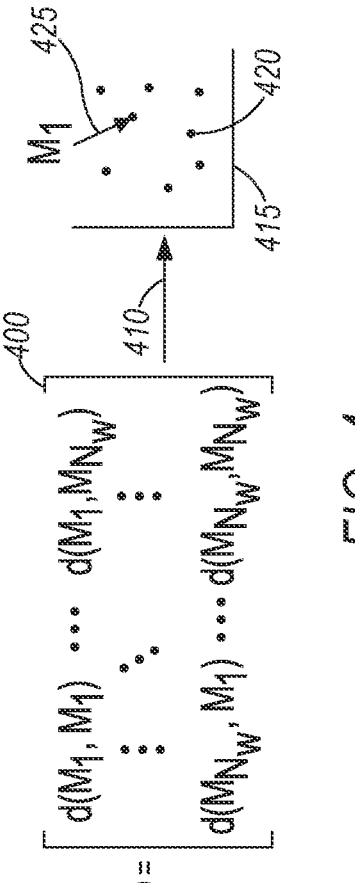
FIG. 4 is a block diagram illustrating a dissimilarity, D, matrix M_{1} corresponding to a time window according to an example embodiment.

FIG. 4 is a block diagram illustrating a dissimilarity, D, matrix M_{1} at 400 corresponding to window 320. A dissimilarity measure d, such as a Frobonius norm, on the space of matrices is shown for each data point, d(M_{1}, M_{1}), . . . , d(M_{1}, M_{N}), . . . , d(M_{N}, M_{1}), . . . , d(M_{N}, M_{N}). For each window the pairwise correlation between it and the other channels is measured, resulting in an N×N correlation matrix. The relationship between each pair of statistical dependence matrices is calculated to obtrain the N×N relationship matrix 400

Finally, the relationship matrix 410 is transformed to obtain an m-dimensional vector for each of the windows as shown at 415, where each dot 420 represents a matrix. Matrix M_{1} is shown for example, at dot 425. The transformation is typically a dimensionality reduction technique, such as multi-dimensional scaling, that provides a vector representation for every statistical dependence matrix. In FIG. 4, the vectors are in 2-dimensional space, but in practice they will be in an "m" dimensional space where "m" depends on the data itself. These vectors are a low dimensional representation of the time series data that may then be used to train a model. Similar vectors may be generated from input data for classification by a trained model.

The choice of statistical dependence between channels (i.e., correlation), the choice of window size, the choice of number of channels (19 in one example), the choice of matrix relationship (i.e., Frobenius), and the choice of dimensionality reduction technique are relatively arbitrary and, in different instances of the problem may be substituted appropriately.

The first feature extraction method is an instance of a more general approach. For example, the dimensionality of the statistical dependence matrices may be reduced before calculating the relationship between their representations.

The dimensionality reduction may be done individually via principal component analysis (PCA) or scaled-Adjacency Spectral Embedding or jointly via an omnibus embedding technique or various multiple adjacency spectral embedding techniques or other multi-graph methods. Reducing the dimensionality of the statistical dependence matrices either individually or jointly generally has a positive impact on downstream inference performance.

The second feature extraction method utilizes the power associated with a set of relevant frequency bands. For an EEG time series, power is associated with the bands [4.1, 5.8], [5.9, 7.4], [7.4, 8.9], [9.0, 11.0], [11.1, 12.9], [13, 19.9], and [20, 25] Hz, corresponding to low-high theta, low-medium-high alpha, and low-high beta frequencies respectively. Time series for other applications may have different types of features, such as power in different sets of frequency bands suitable for the particular application.

The power bands for each channel are normalized such that the features for a particular channel sum to 1. Thus, for each time window, a two-dimensional (number of channels by number of bands) feature matrix is generated. The matrix is flattened into a single, number-of-channels-times-number-of-bands length feature vector. Finally, because 19(7)=133-dimensional space is relatively large given the relatively small amount of training data used, the feature vector is projected into a four-dimensional space. The projection (and its dimension) may be learned via PCA (or another dimensionality reduction technique) of the available training data.

In various examples, the trained model may be used for local detection in real time of a length of time a person has a stressful mental load. Such detection can help determine how much energy is spent performing a task. Longer periods of stress can induce elevated stress as well as decrease cognitive performance. Such detection may be used to prevent operation of heavy equipment, either manually or automatically.

In a streaming, real time example, with data being collected on a person, the feature vectors may be generated and pushed through the trained model to determine whether not a person is stressed.

In further examples, other sets of time series data may have different associated labels, such as occupied/unoccupied, interested/not interested, safe/unsafe, well, fatigued/not fatigued. Note that the labels need not be binary but can alternatively be multi-class.

The example dataset used above has labels applied by the researchers based on the task, or no task, being performed at the times of the measurements. Thus, the label is task based. Other types of tasks or observed human conditions, such as fatigued/not fatigued may be generated by human observation or even subject observations for further labeled datasets.

Figure 5:
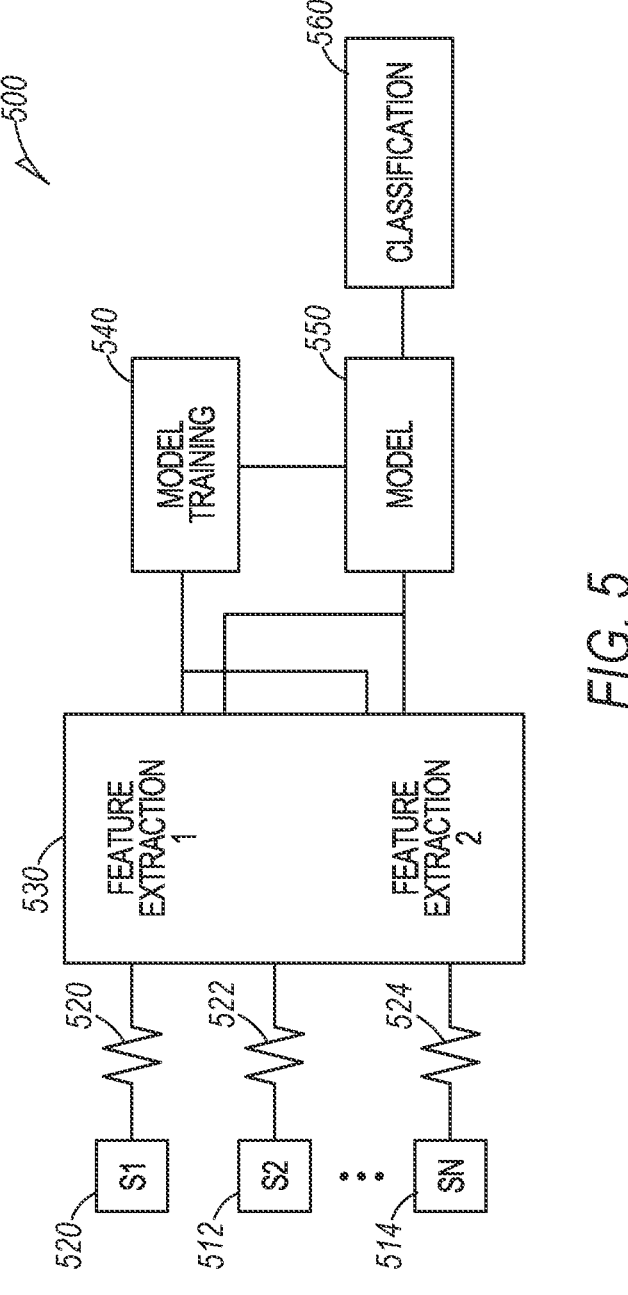
FIG. 5 is a block diagram of a system for extracting features from multivariate time series data to extract efficient feature vectors to both train a model and classify input multivariate time series data from which feature vectors have been extracted according to an example embodiment.

FIG. 5 is a block diagram of a computer implemented method 500 for extracting multiple types of features, always including the features described in method 100 and method 200, from a set of biosensors. Multiple sensors 510, 512, and 514 are shown collecting data, such as EEG data, ECG data or other biologically derived signal, and providing corresponding signals 520, 522, and 524 to a feature extractor 530.

Feature extractor 530 includes measures of statistical dependence amongst the sensors as described in Operation 100.

The model is trained at operation 540 using the learned features and saved at operation 550 as is done in operation 160.

Once the model is trained and saved, previously unseen multi-variate time series can be processed analogously, and the machine learning model 550 can be used to make predictions.

While FIG. 5 illustrates two types of feature extraction it is possible to include more, though always including the method outlined in Operation 100 and Operation 200.

Figure 6:
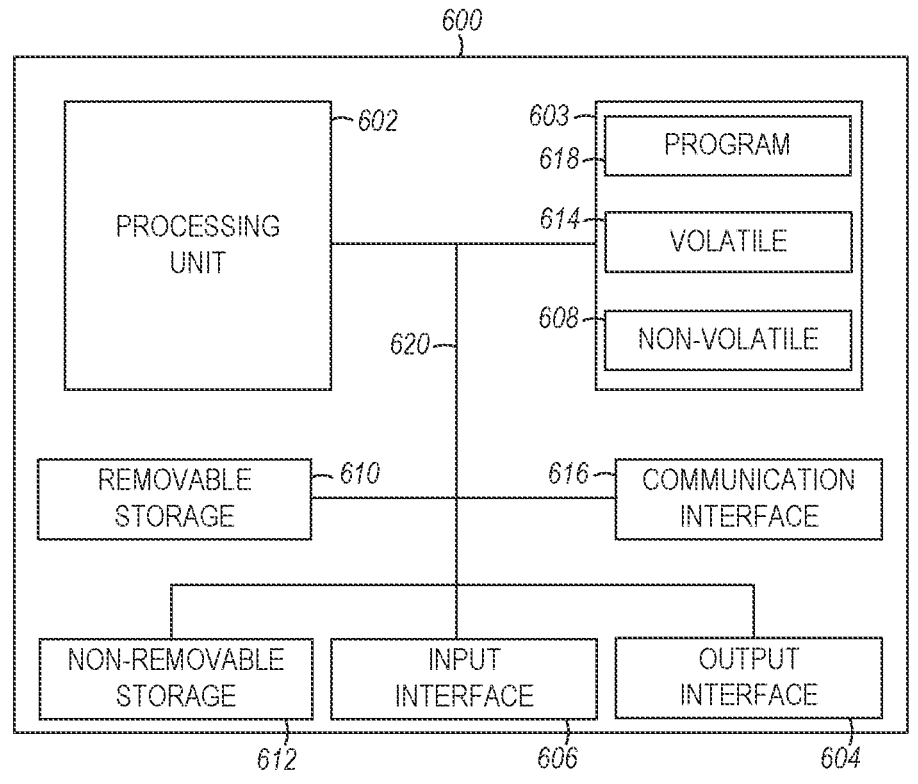
FIG. 6 is a block schematic diagram of a computer system to implement one or more example embodiments.

FIG. 6 is a block schematic diagram of a computer system 600 to generate feature vectors having reduced dimensionality for time series data and for performing methods and algorithms according to example embodiments. All components need not be used in various embodiments.

One example computing device in the form of a computer 600 may include a processing unit 602, memory 603, removable storage 610, and non-removable storage 612. Although the example computing device is illustrated and described as computer 600, the computing device may be in different forms in different embodiments. For example, the computing device may instead be a smartphone, a tablet, smartwatch, smart storage device (SSD), or other computing device including the same or similar elements as illustrated and described with regard to FIG. 6. Devices, such as smartphones, tablets, and smartwatches, are generally collectively referred to as mobile devices or user equipment.

Although the various data storage elements are illustrated as part of the computer 600, the storage may also or alternatively include cloud-based storage accessible via a network, such as the Internet or server-based storage. Note also that an SSD may include a processor on which the parser may be run, allowing transfer of parsed, filtered data through I/O channels between the SSD and main memory.

Memory 603 may include volatile memory 614 and non-volatile memory 608. Computer 600 may include—or have access to a computing environment that includes—a variety of computer-readable media, such as volatile memory 614 and non-volatile memory 608, removable storage 610 and non-removable storage 612. Computer storage includes random access memory (RAM), read only memory (ROM), erasable programmable read-only memory (EPROM) or electrically erasable programmable read-only memory (EEPROM), flash memory or other memory technologies, compact disc read-only memory (CD ROM), Digital Versatile Disks (DVD) or other optical disk storage, magnetic cassettes, magnetic tape, magnetic disk storage or other magnetic storage devices, or any other medium capable of storing computer-readable instructions.

Computer 600 may include or have access to a computing environment that includes input interface 606, output interface 604, and a communication interface 616. Output interface 604 may include a display device, such as a touchscreen, that also may serve as an input device. The input interface 606 may include one or more of a touchscreen, touchpad, mouse, keyboard, camera, one or more device-specific buttons, one or more sensors integrated within or coupled via wired or wireless data connections to the computer 600, and other input devices. The computer may operate in a networked environment using a communication connection to connect to one or more remote computers, such as database servers. The remote computer may include a personal computer (PC), server, router, network PC, a peer device or other common data flow network switch, or the like. The communication connection may include a Local Area Network (LAN), a Wide Area Network (WAN), cellular, Wi-Fi, Bluetooth, or other networks. According to one embodiment, the various components of computer 600 are connected with a system bus 620.

Computer-readable instructions stored on a computer-readable medium are executable by the processing unit 602 of the computer 600, such as a program 618. The program 618 in some embodiments comprises software to implement one or more methods described herein. A hard drive, CD-ROM, and RAM are some examples of articles including a non-transitory computer-readable medium such as a storage device. The terms computer-readable medium, machine readable medium, and storage device do not include carrier waves or signals to the extent carrier waves and signals are deemed too transitory. Storage can also include networked storage, such as a storage area network (SAN). Computer program 618 along with the workspace manager 622 may be used to cause processing unit 602 to perform one or more methods or algorithms described herein.

Examples

1. A computer implemented method includes accessing a multivariate time series set of samples collected by multiple biological sensors sensing a first biological function over a first period of time, dividing the data set into windows, calculating statistical dependencies between the samples of the timeseries data collected by each sensor, generating a relationship matrix as a function of a relationships between the statistical dependencies, and transforming the relationship matrix to generate a first feature vector for each window of time that captures the statistical dependencies amongst the sensors.

2. The method of example 1 and further includes training a machine learning model based on the first feature vectors as training data.

3. The method of example 2 wherein the training data includes labels for the first feature vectors.

4. The method of any of examples 2-3 and further including receiving input multivariate time series data collected by multiple biological sensors, generating input feature vectors in the same manner as the first feature vectors, and classifying the input feature vectors via the trained machine learning model.

5. The method of any of examples 1-4 and further including generating a second feature vector based on power associated with frequency bands of the samples.

6. The method of example 5 and further including training a machine learning model based on the first and second feature vectors as training data.

7. The method of example 6 wherein the training data includes labels for the first and second feature vectors.

8. The method of any of examples 1-7 wherein the samples include biological data from humans.

9. The method of example 8 wherein the samples include EEG data and the sensors include electrodes electrically coupled to a human skull.

10. The method of any of examples 1-9 wherein generating a relationship matrix includes calculating differences between each pair of statistical dependence matrices.

11. The method of example 10 wherein the relationship is set to a constant as a function of a threshold.

12. The method of any of examples 1-11 and further including generating a second feature vector representative of a different sensed parameter.

13. The method of example 13 and further including generating at least one additional feature vector, each representative of a further different sensed parameter.

14. The method of example 14 and further including training a machine learning model based on the first, second, and at least one additional feature vectors as training data.

15. A machine-readable storage device has instructions for execution by a processor of a machine to cause the processor to perform operations to perform any of the methods of examples 1-14.

16. A device includes a processor and a memory device coupled to the processor and having a program stored thereon for execution by the processor to perform operations to perform any of the methods of examples 1-14.

Although a few embodiments have been described in detail above, other modifications are possible. For example, the logic flows depicted in the figures do not require the particular order shown, or sequential order, to achieve desirable results. Other steps may be provided, or steps may be eliminated, from the described flows, and other components may be added to, or removed from, the described systems. Other embodiments may be within the scope of the following claims.

The invention claimed is:

1. A computer implemented method comprising:
accessing a multivariate time series set of samples collected by multiple (N) biological sensors sensing a first biological function over a first period of time;
dividing the data set into non-overlapping windows of time;
calculating statistical dependencies for each pair of sensors between the samples of the timeseries data collected by each sensor;
generating an N×N relationship matrix as a function of the statistical dependencies for each pair of sensors;
transforming the relationship matrix using a dimensionality reduction technique to generate a first feature vector for each window of time that captures the statistical dependencies amongst the sensors;
training a machine learning model based on the first feature vectors comprising training data;
receiving input multivariate time series data collected by multiple biological sensors;
generating input feature vectors in the same manner as the first feature vectors; and
classifying the input feature vectors via the trained machine learning model.

2. The method of claim 1 wherein the training data includes labels for the first feature vectors.

3. The method of claim 1 and further comprising generating a second feature vector based on power associated with frequency bands of the samples.

4. The method of claim 3 wherein the machine learning model is further trained based on the first and second feature vectors comprising training data.

5. The method of claim 4 wherein the training data includes labels for the first and second feature vectors.

6. The method of claim 1 wherein the samples comprise biological data from humans.

7. The method of claim 6 wherein the samples comprise EEG data and the sensors comprise electrodes.

8. The method of claim 1 wherein generating a distance matrix comprises calculating differences between each statistical dependence.

9. The method of claim 8 wherein the differences are set to a constant as a function of a threshold.

10. The method of claim 1 and further comprising generating a second feature vector representative of a different sensed parameter.

11. The method of claim 10 and further comprising generating at least one additional feature vector, each representative of a further different sensed parameter.

12. The method of claim 3 and further comprising training a machine learning model based on the first, second, and at least one additional vectors comprising training data.

13. A machine-readable storage device having instructions for execution by a processor of a machine to cause the processor to perform operations to perform a method, the operations comprising:

accessing a multivariate time series set of samples collected by multiple (N) biological sensors sensing a first biological function over a first period of time;

dividing the data set into non-overlapping windows of time;

calculating statistical dependencies for each pair of sensors between the samples of the timeseries data collected by each sensor;

generating an N×N relationship matrix as a function of the statistical dependencies for each pair of sensors;

transforming the relationship matrix using a dimensionality reduction technique to generate a first feature vector for each window of time that captures the statistical dependencies amongst the sensors;

training a machine learning model based on the first feature vectors comprising training data:

receiving input multivariate time series data collected by multiple biological sensors;

generating input feature vectors in the same manner as the first feature vectors; and classifying the input feature vectors via the trained machine learning model.

14. The device of claim 13, wherein the training data includes labels for the first feature vectors.

15. The device of claim 13, the operations further comprising generating a second feature vector based on power associated with frequency bands of the samples and wherein the machine learning model is trained based on the first and second feature vectors comprising training data that includes labels for the first and second feature vectors.

16. A device comprising:

a processor; and a memory device coupled to the processor and having a program stored thereon for execution by the processor to perform operations comprising:

accessing a multivariate time series set of samples collected by multiple (N) biological sensors sensing a first biological function over a first period of time;

dividing the data set into non-overlapping windows of time;

calculating statistical dependencies for each pair of sensors between the samples of the timeseries data collected by each sensor;

generating an N×N relationship matrix as a function of the statistical dependencies for each pair of sensors;

transforming the relationship matrix using a dimensionality reduction technique to generate a first feature vector for each window of time that captures the statistical dependencies amongst the sensors;

training a machine learning model based on the first feature vectors comprising training data;

receiving input multivariate time series data collected by multiple biological sensors;

generating input feature vectors in the same manner as the first feature vectors; and classifying the input feature vectors via the trained machine learning model.

* * * * *